(12) United States Patent
Rockweiler et al.

(10) Patent No.: US 10,543,382 B2
(45) Date of Patent: Jan. 28, 2020

(54) DEVICE AND METHOD TO TREAT VAGINAL ATROPHY

(71) Applicant: THE BOARD OF TRUSTEES OF THE LELAND STANFORD JUNIOR UNIVERSITY, Stanford, CA (US)

(72) Inventors: Holly Elizabeth Rockweiler, Portland, OR (US); Ryan Taylor Krone, Portland, OR (US); Jonathan Daniel Steinberger, Portland, OR (US); Kathryn Olson, Redwood City, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 234 days.

(21) Appl. No.: 15/111,099

(22) PCT Filed: Jan. 26, 2015

(86) PCT No.: PCT/US2015/012825
§ 371 (c)(1),
(2) Date: Jul. 12, 2016

(87) PCT Pub. No.: WO2015/116512
PCT Pub. Date: Aug. 6, 2015

(65) Prior Publication Data
US 2016/0346568 A1   Dec. 1, 2016

Related U.S. Application Data

(60) Provisional application No. 61/933,712, filed on Jan. 30, 2014, provisional application No. 61/947,715, (Continued)

(51) Int. Cl.
*A61N 7/00* (2006.01)
*A61B 5/01* (2006.01)
(Continued)

(52) U.S. Cl.
CPC .............. *A61N 7/00* (2013.01); *A61B 5/01* (2013.01); *A61B 5/026* (2013.01); *A61B 5/4294* (2013.01);
(Continued)

(58) Field of Classification Search
CPC ........................................... A61N 7/00
See application file for complete search history.

(56) References Cited

U.S. PATENT DOCUMENTS

| 3,504,665 A | 4/1970 | Bakunin et al. |
| 4,646,725 A | 3/1987 | Moasser |

(Continued)

FOREIGN PATENT DOCUMENTS

| CN | 1778414 A | 5/2006 |
| CN | 102397633 A | 4/2012 |

(Continued)

OTHER PUBLICATIONS

Baker et al.; The effect of therapeutic modalities on blood flow in the human calf; Journal of Orthopaedic and sports Physical Therapy; 13(1); pp. 23-27; Jan. 1991.
(Continued)

*Primary Examiner* — Rochelle D Turchen
(74) *Attorney, Agent, or Firm* — Shay Glenn LLP

(57) ABSTRACT

A method of treating vaginal tissue atrophy in a female subject, the method including the steps of engaging an energy delivery element with tissue in or around the subject's vagina; applying energy to the tissue from the energy delivery element; and increasing blood flow to internal vaginal tissue to an increased level above a baseline level of blood flow to the internal vaginal tissue, the increased level of blood flow to the internal vaginal tissue persisting after the applying step ceases. The invention also provides devices for performing this therapy.

23 Claims, 10 Drawing Sheets

Related U.S. Application Data filed on Mar. 4, 2014, provisional application No. 61/982,475, filed on Apr. 22, 2014.

(51) Int. Cl.
 *A61B 5/026* (2006.01)
 *A61B 5/00* (2006.01)
 *A61B 17/225* (2006.01)

(52) U.S. Cl.
 CPC .......... *A61B 5/4337* (2013.01); *A61B 5/4836* (2013.01); *A61B 2017/2253* (2013.01); *A61N 2007/0043* (2013.01)

(56) References Cited

U.S. PATENT DOCUMENTS

| | | | |
|---|---|---|---|
| 4,757,820 | A | 7/1988 | Itoh |
| 4,938,217 | A | 7/1990 | Lele |
| 5,827,203 | A | 10/1998 | Nita |
| 6,169,914 | B1 | 1/2001 | Hovland et al. |
| 6,221,021 | B1 | 4/2001 | Redano |
| 6,741,895 | B1 | 5/2004 | Gafni et al. |
| 2002/0068900 | A1 | 6/2002 | Barnes et al. |
| 2002/0091339 | A1 | 7/2002 | Horzewski et al. |
| 2005/0049509 | A1 | 3/2005 | Mansour et al. |
| 2005/0203399 | A1 | 9/2005 | Vaezy et al. |
| 2005/0216069 | A1 | 9/2005 | Cohen et al. |
| 2005/0222273 | A1* | 10/2005 | Dodd .................. A61K 31/085 514/681 |
| 2006/0100552 | A1† | 5/2006 | Schultheiss |
| 2006/0235303 | A1 | 10/2006 | Vaezy et al. |
| 2007/0021809 | A1 | 1/2007 | Cole et al. |
| 2007/0179413 | A1 | 8/2007 | Imboden et al. |
| 2007/0197918 | A1 | 8/2007 | Vitek et al. |
| 2009/0043248 | A1 | 2/2009 | Peterson et al. |
| 2011/0040187 | A1 | 2/2011 | Matsumura |
| 2011/0313293 | A1 | 12/2011 | Lindekugel et al. |
| 2012/0065501 | A1 | 3/2012 | Dae et al. |
| 2012/0143062 | A1 | 6/2012 | Nordgren et al. |
| 2013/0303904 | A1† | 11/2013 | Barthe |
| 2013/0338545 | A1 | 12/2013 | Azhari et al. |
| 2014/0163437 | A1 | 6/2014 | Mack et al. |
| 2014/0257145 | A1 | 9/2014 | Emery |
| 2015/0135840 | A1 | 5/2015 | Sato et al. |
| 2017/0143997 | A1 | 5/2017 | Rockweiler et al. |

FOREIGN PATENT DOCUMENTS

| | | |
|---|---|---|
| WO | WO2007/092610 A2 | 8/2007 |
| WO | WO2011/082402 A2 | 7/2011 |
| WO | WO2013/048912 A2 | 4/2013 |
| WO | WO2013/184798 A1 | 12/2013 |

OTHER PUBLICATIONS

Bishop et al.; Human tissue—temperature rise during ultrasound treatments with the aquaflex gel pad; Journal of Athletic Training; 39(2); pp. 126-131; Apr. 1, 2004.

breastcancer.org; U.S. breast cancer statistics; 2 pages; retrieved from the internet (http://www.breastcancer.org/symptoms/understand_bc/statistics); Last Modified Jun. 23, 2016.

Chin et al.; Prevalence and severity of urogenital symptoms in postmenopausal women receiving endocrine therapy for breast cancer; Clinical Breast Cancer; 9(2); pp. 108-117; May 31, 2009.

Committee on Practice Bulletins _ Gynecology; ACOG Practice Bulletin No. 126: Management of gynecologic issues in women with breast cancer; Obstet Gynecol.; 119(126); pp. 666-682; Mar. 2012.

Dalecki; Mechanical bioeffects of ultrasound; Annu. Rev. Biomed. Eng.; 6; pp. 229-248; Aug. 15, 2004.

Ferguson; Ultrasound in the treatment of surgical wounds; Physiotherapy; 67(2); p. 43; Feb. 10, 1981.

Hutchinson et al.; Intracavitary ultrasound phased arrays for non-invasive prostate surgery; IEEE transactions on ultrasonics, Ferroelectrics, and Frequency Control; 43(6); pp. 1032-1042; Nov. 1996.

Kingberg et al.; Vulvar and vaginal atrophy in postmenopausal women: findings from the revive (REal Women's Views of Treatment Options for Menopausal Vaginal changEs) survey; The Journal of Sexual Medicine; 10(7); pp. 1790-1799; Jul. 1, 2013.

Lloyd et al.; Female genital appearance: 'normality' unfolds*; BJOG: an International Journal of Obstetrics and Gynaecology; 112; pp. 643-646; May 2005.

Noble; Physical therapy in gyn: Ultrasound postpartum; 2 pgs.; (this information available to applicant(s) at least as of Jan. 14, 2015).

Nyborg; Biological effects of ultrasound: development of safety guidelines. Part II: general review; Ultrasound in Med. & Biol.; 27(3); pp. 301-333; Mar. 31, 2001.

Rossouw et al.; Risks and benefits of estrogen plus progestin in healthy postmenopausal women: principal results from the women's health initiative randomized controlled trial; JAMA; 288(3); pp. 321-333; Jul. 17, 2002.

Soneson; HIFU simulator v1.2 user's manual; US Food and Drug Administration; 17 pages; Jan. 30, 2011.

Szabo; Ultrasound imaging: inside out, 2nd Edition; Chapter 5: Transducers; pp. 122-165; Academic Press; (year of pub. sufficiently earlier than effective US filing date and any foreign priority date) 2004.

Young et al.; The effect of therapeutic ultrasound on angiogenesis; Ultrasound in Med. & Biol.; 16(3); pp. 261-269; Jan. 1, 1990.

Cao et al.; Measurements of female genital appearance in chinese adults seeking genital cosmetic surgery: a preliminary report from a gynecological center; Int. Urogynecol.; 26(5); pp. 729-735; Nov. 2014 (online).

Michlovitz et al.; Modalities for therapeutic intervention (contemporary perspectives in rehabilitation); 5th Edition; F.A. Davis Company; Chapter 5 Therapeutic Ultrasound; p. 91-92; Jun. 21, 2011.

Krone et al.; U.S. Appl. No. 15/767,286 entitled "Ultrasound device for vulvovaginal rejuvenation," filed Apr. 10, 2018.

\* cited by examiner
† cited by third party

DEVICE AND METHOD TO TREAT VAGINAL ATROPHY

CROSS REFERENCE TO RELATED APPLICATIONS

This application claims the benefit of U.S. Provisional Patent Application No. 61/933,712 (filed Jan. 30, 2014); U.S. Provisional Patent Application No. 61/947,715 (filed Mar. 4, 2014); and U.S. Provisional Patent Application No. 61/982,475 (filed Apr. 22, 2014), each of which is incorporated by reference in its entirety.

This invention was made with Government support under contract TR001085 awarded by the National Institutes of Health. The Government has certain rights in the invention.

INCORPORATION BY REFERENCE

All publications and patent applications mentioned in this specification are incorporated herein by reference in their entirety to the same extent as if each individual publication or patent application was specifically and individually indicated to be incorporated by reference.

BACKGROUND

The prior art has a variety of devices and methods directed to female sexual functioning and response. Many of these devices are designed to provide sexual pleasure to women with normally functioning sexual response.

In some women, sexual response is less than normal or totally absent. For example, estrogen-deficient women may experience vaginal discomfort during intercourse due to reduced lubrication and reduced resilience of vaginal tissue. Over time, atrophy of vaginal tissue may worsen, thereby diminishing sexual response even further.

The prior art also includes devices and methods to treat disorders of the female sex organs. For example, U.S. Pat. No. 6,741,895 describes a vaginal probe that applies heat, vibration, electrical stimulation and/or pressure to vaginal nerves to treat female sexual dysfunction. US 2007/0021809 describes devices and methods that apply topical heating or cooling to treat inflammation or irritation of a woman's genitals. There is no data showing that any of these prior art devices and methods provides a lasting benefit to women experiencing vaginal atrophy or other diminished sexual function, however.

SUMMARY OF THE DISCLOSURE

The invention provides devices and methods for improving the health of vaginal tissue (e.g., through increasing vaginal blood flow) by applying energy, such as ultrasound energy, to tissue in and around the vagina. The benefits of this energy application persist after the energy application ceases; the therapy therefore provides an effective treatment for vaginal atrophy.

In particular, the invention provides methods and devices for increasing blood flow, lubrication, elasticity and resilience of the vagina and surrounding tissue in, e.g., estrogen-deficient women and/or women with vaginal atrophy or discomfort. According to the invention, energy is introduced locally into the woman's genital tissue. The applied energy may be chemical energy, electrical energy, ultrasound energy, RF energy, suction, photonic energy, electromagnetic radiation or light-based (e.g., pulsed or continuous laser). The energy may be applied intravaginally, near the vulva without penetrating the vagina, or outside the subject's body.

One aspect of the invention provides a method of treating vaginal tissue atrophy in a female subject. In some embodiments, the method includes the steps of: engaging an energy delivery element with tissue in or around the subject's vagina; applying energy to the tissue from the energy delivery element; and increasing blood flow to internal vaginal tissue to an increased level above a baseline level of blood flow to the internal vaginal tissue, the increased level of blood flow to the internal vaginal tissue persisting after the applying step ceases.

In some embodiments, the energy applied by the energy delivery element is ultrasound energy delivered, e.g., at a frequency between 0.5 MHz and 4 MHz, an intensity between 0.25 W/cm$^2$ and 5 W/cm$^2$ and/or at a duty cycle in a range of 20%-80%. In these embodiments, the energy delivery element may include an ultrasound probe and/or an ultrasound coupling medium. In these methods, the energy may be applied for a period between 30 seconds and 6 hours.

In some embodiments of the method, the engaging step includes the step of engaging the energy delivery element, such as the ultrasound coupling medium, with tissue exterior to the subject's vagina. Alternatively or additionally, the engaging step may include the step of engaging the energy delivery element with tissue inside the subject's vagina. In some embodiments, the engaging step may include the step of engaging the energy delivery element with tissue of the subject's abdomen or pelvis.

In some embodiments, the method includes the step of measuring a physiologic parameter of the subject's tissue in or around the subject's vagina and controlling energy delivery from the energy delivery element based on the measured parameter. The measured physiologic parameter may be, e.g., temperature, blood flow or vaginal lubrication.

Another aspect of the invention provides a device for treating vaginal tissue atrophy in a female subject. The device may have an energy delivery element adapted to engage tissue in or around the subject's vagina and an energy source adapted to deliver energy to the energy delivery element to increase blood flow to internal vaginal tissue to an increased level above a baseline level of blood flow to the internal vaginal tissue such that the increased level of blood flow to the internal vaginal tissue persists after energy application ceases.

In some embodiments, the energy applied by the energy delivery element is ultrasound energy delivered, e.g., at a frequency between 0.5 MHz and 4 MHz, an intensity between 0.25 W/cm$^2$ and 5 W/cm$^2$ and/or at a duty cycle in a range of 20%-80%. In these embodiments, the energy delivery element may include an ultrasound probe and/or an ultrasound coupling medium.

In some embodiments, the ultrasound coupling medium is disposed within a container adapted to cover a vaginal opening and tissue around the vaginal opening. The container may be adapted to conform to the subject's tissue. In some embodiments, the ultrasound coupling medium includes a gel on a surface of the energy delivery element.

In various embodiments the energy delivery element may be adapted to engage tissue exterior to the subject's vagina and/or inside the subject's vagina. In some embodiments the energy delivery element may be adapted to engage tissue of the subject's abdomen or pelvis.

In some embodiments the device includes a sensor adapted and configured to measure a physiologic parameter of tissue in or around the subject's vagina when the energy delivery element is engaged with tissue in or around the subject's vagina, with the device being further configured to use information from the sensor to control energy delivery from the energy delivery element. The measure physiologic parameter may be, e.g., temperature, blood flow or vaginal lubrication.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

The invention provides methods and devices that can be used to increase blood flow, lubrication, elasticity and resilience of the vagina and surrounding tissues in estrogen-deficient women (from natural causes or from the consequences of medical therapies), in women with vaginal atrophy, and/or in women who experience vaginal discomfort, whether constantly or specifically during sexual intercourse. In some embodiments, the device applies energy locally to genital tissue (e.g., vaginal tissue) to increase blood flow to the genital area and to improve and/or prevent deterioration of tissue health and natural lubrication. The methods and devices may also improve the symptoms of female sexual dysfunction.

In some embodiments, energy (including but not limited to thermal energy, mechanical energy, electrical energy, electromagnetic energy, radiofrequency energy, ultrasound energy and chemical energy) is applied to the walls of the vagina from an external source via, e.g., conductive, inductive, radiative or convective heat transfer to the tissue.

Figure 1:
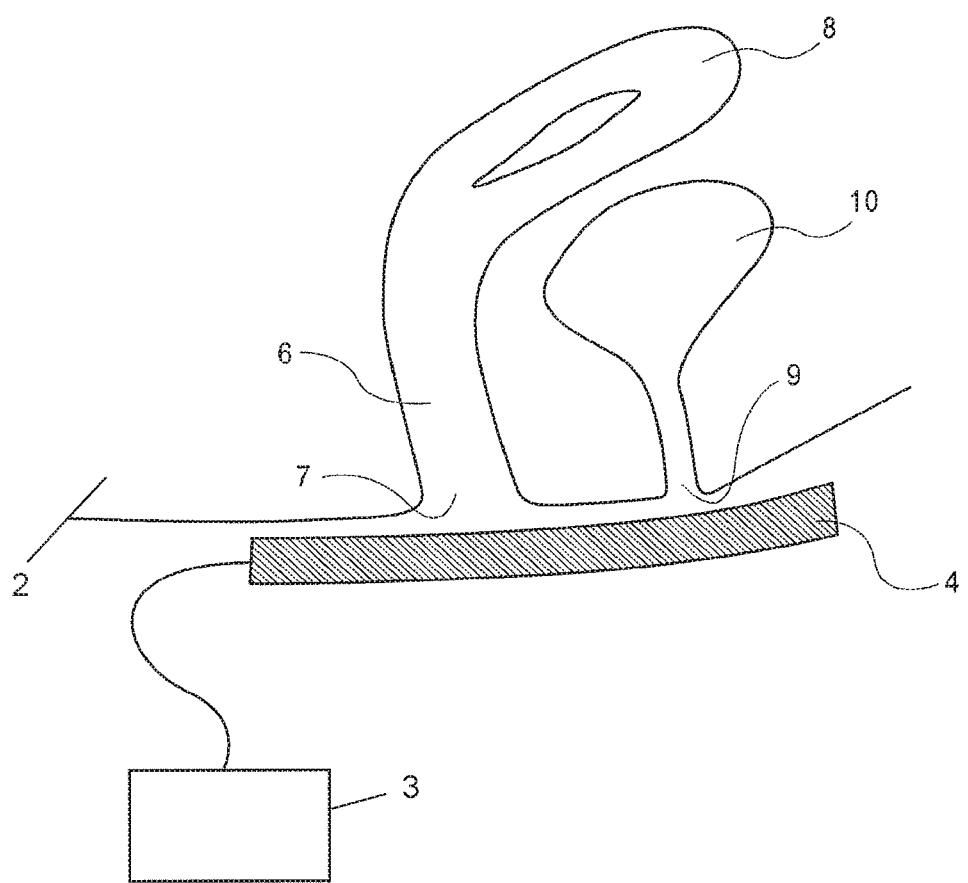
FIG. 1 is a cross-sectional view of an embodiment of the invention in position on a subject.
Figure 2:
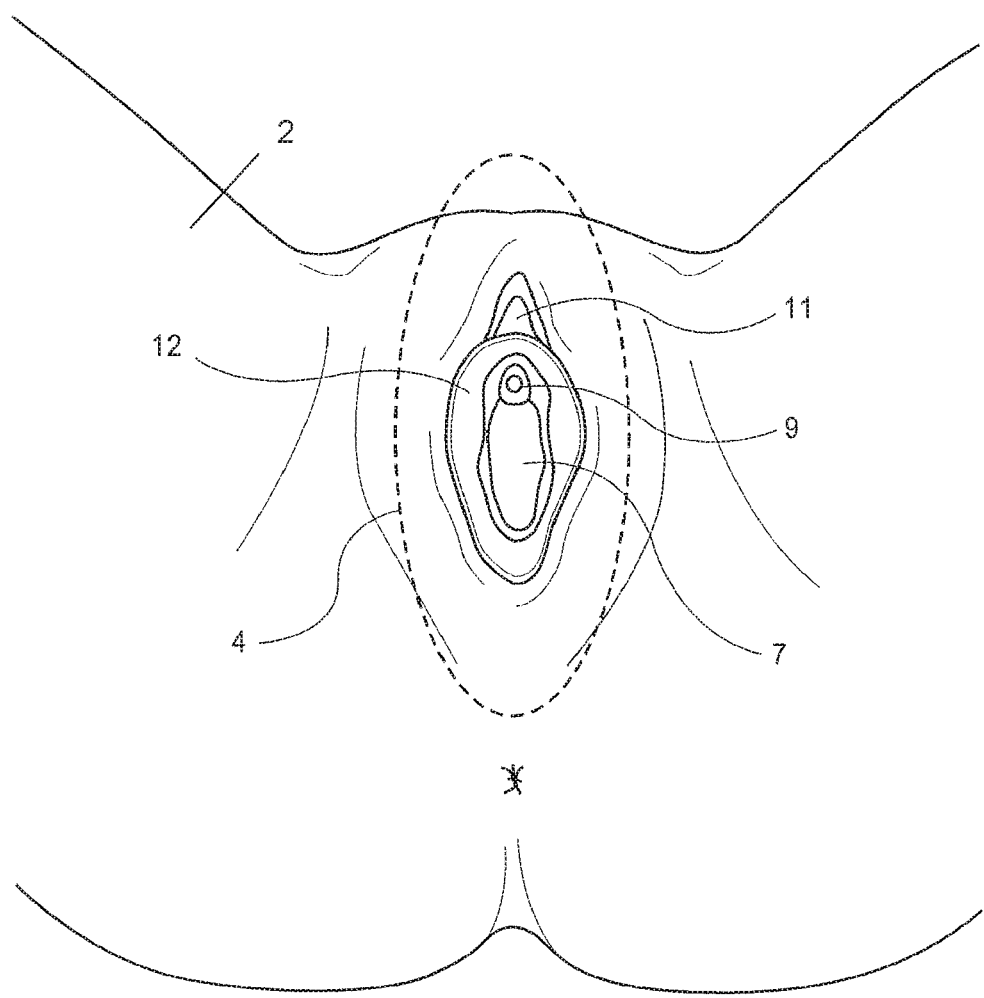
FIG. 2 is an elevational view showing position of the device of FIG. 1 on the subject.

FIGS. 1 and 2 show one embodiment of a device according to an embodiment of the invention. The device includes an energy delivery element 4 adapted to engage tissue around the opening 7 of the vagina 6 of the subject 2. Also shown in these figures are the subject's uterus 8, bladder 10, urethral opening 9, vulva 12 and clitoris 11. As shown in cross-section in FIG. 1 and in phantom in FIG. 2, in this embodiment energy delivery element 4 engages only exterior genital tissue (to avoid irritation of sensitive vaginal tissue) and covers the subject's vulva 12, clitoris 11, urethral opening 9 and vaginal opening 7. Other embodiments could cover more or less of the subject's genitalia and/or the subject's mons pubis or proximal thighs. In this embodiment, energy delivery device is connected to an energy source 3, such as an ultrasound generator.

According to methods of this invention, energy may be applied from energy source 3 through energy delivery element 4 to the patient's genitalia on an acute basis or on a regular basis, such as daily or weekly. In some embodiments, the energy delivery element may be incorporated into underwear. In some embodiments, the energy delivery element may be attached directly to the subject's body and held in place by suction, adhesives or other securing mechanisms. The energy delivery element may be reusable or disposable.

In some embodiments, the energy source may be combined with the energy delivery element. In some embodiments, the energy delivery element is flexible and may include flexible circuitry.

Figure 3:
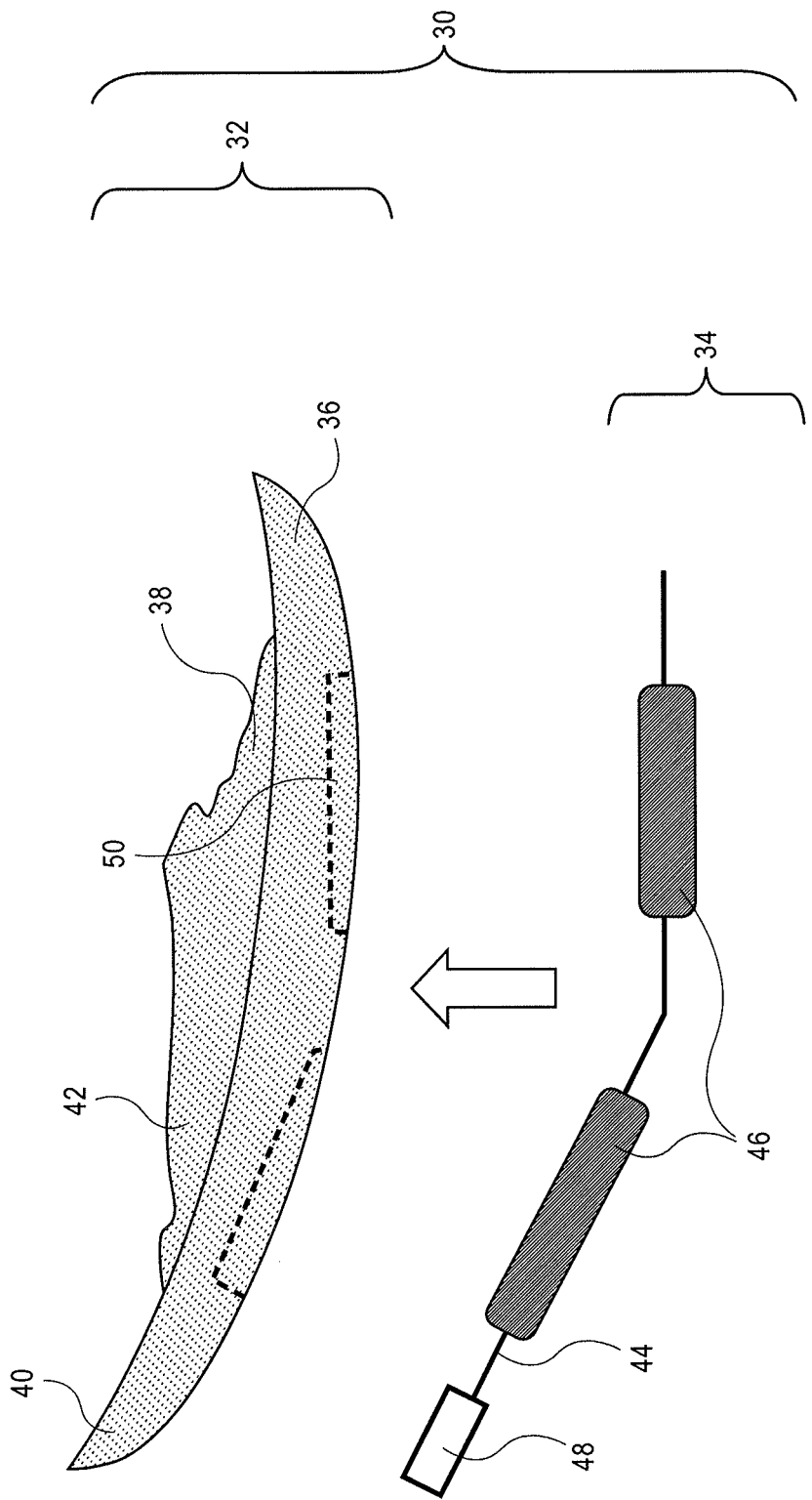
FIG. 3 is an exploded view of another embodiment of a device according to the invention.

FIG. 3 shows in an exploded view an embodiment of the device of this invention adapted to delivery ultrasound energy to tissue around a subject's vagina (such as the vulva and introitus) to increase blood flow in vaginal tissue. The energy delivery element 30 is designed to be applied completely externally without penetrating the vagina to avoid irritation of sensitive vaginal tissue. Energy delivery element 30 has a coupling pad 32 and a transducer assembly 34; both of these elements may be reusable or disposable.

The coupling pad 32 has a main structure 36 and a coupling structure 38. Main structure 36 may be deformable, yet rigid enough to support the coupling structure 38. Main structure 36 may be formed from two plates or sections connected together. In one embodiment, a top plate (not shown) has a cut-out (not shown) to accommodate the coupling structure 38, and a bottom plate 40 has cut-outs 42 to accommodate connection to the ultrasound transducer 34. Main structure 36 may be formed from biocompatible or non-allergenic materials such as silicone rubber, soft plastics, fabrics or flexible foams.

Main structure 36 is configured to attach to the subject's body in a manner that maintains intimate contact between the coupling structure 38 and tissue around the subject's vagina, such as the vulva. Attachment mechanisms (not shown) such as straps or tensile supports wrapping around the subject's waist, double-stick tape, glue or other adhesive (including temperature-sensitive adhesive) can be used to attach the main structure to the subject's body. The attachment mechanism may also employ an element inserted into the subject's vaginal opening or anus. The subject's underwear can also be used instead of, or in addition to, such attachment mechanisms, in the manner of a panty liner. Projections, wing-like features, adhesive strips, materials attachable to tissue with static electricity, or Velcro® hook and loop fasteners may also be used. The attachment mechanism may also employ suction to maintain contact between the coupling structure and the subject's skin.

Main structure 36 may be shaped, e.g., as a rectangle or as a contoured and filled-out figure eight (e.g., like a feminine hygiene pad). Main structure 36 may be shaped to fit in the subject's underwear. Main structure 36 may be omitted entirely if another supporting structure is use, such as, e.g., by building the coupling structure into underwear worn by the subject.

The coupling structure 38 can be a solid, but soft, deformable structure that conforms to the subject's vulva. In some embodiments, the coupling structure is entirely external to the vaginal canal; vaginal penetration may irritate sensitive vaginal tissue or cause discomfort for women with atrophy or vaginal discomfort. The coupling structure 38 ensures safe and effective energy delivery to vaginal tissue. The conforming design of the coupling structure prevents skin burns and ensures appropriate energy conduction between the transducer and the target vaginal tissue by minimizing air pockets between the two surfaces.

In one embodiment, coupling structure 38 is convex and shaped to conform to the subject's vulva and introitus (e.g., elliptical or ovoid). Coupling structure 38 is formed from biocompatible, easily deformable and sonolucent material, such as gels like pectin, gelatin, low-durometer rubbers, low-durometer silicone or other non-porous soft materials. In some embodiments, the coupling structure is a deformable container containing a fluid or semi-solid such as water (e.g., deionized water, distilled water), oil (e.g., mineral oil), gel, gelatin or other sonolucent and biocompatible fluid or semi-solid. The container may be made from silicone, PTFE, nylon, HDPE or other plastic.

In some embodiments, coupling gel (not shown) is placed between the coupling structure 38 and the subject's skin to enhance acoustic coupling with the subject's tissue. The gel may be pre-applied to the coupling structure at the time of manufacture and covered with a protective strip or other covering that is removed at the time of use. The gel may also be applied to the coupling structure by the user at the time of use.

In some embodiments, the transducer assembly 34 includes a damping back plate 44 made, e.g. of semi-deformable, biocompatible or non-allergenic material(s) such as, e.g., polymers like HDPE, PEEK, acrylic, polyethylene or nylon. Transducer assembly 34 also has one or an array of piezo-ceramic or CMUT ultrasound transducers 46 to apply diffuse or focused ultrasound energy to the tissue around the subject's vagina through coupling pad 32. The transducer assembly 34 may have wire leads and a plug or other interface 48 that can connect the transducer(s) 46 to an ultrasound generator (not shown). In other embodiments, the transducer(s) 46 can connect to a generator wirelessly.

When the device is assembled for use, the transducers 46 are oriented with respect to coupling pad 32 to ensure the vulva and/or introitus are in the appropriate acoustic field and the ultrasound waves penetrate to the target vaginal tissue and appropriate vascular bed. (In some embodiments, the target of the ultrasound energy (unfocused or focused) may be further tuned to cover the lower third of the vaginal canal.) The orientation between the transducers 46 and coupling pad 32 can be achieved with geometric features 50 that mate between the transducers 46 (or other part of the transducer assembly 34) and the backing plate 36 of coupling pad 32, such as a key and slot arrangement, a pin and hole arrangement, etc. The orientation can also be achieved through the design of the coupling structure 38. The orientation of the transducers can be tuned for each subject's anatomy, either manually (e.g., through different size options) or though automatic transducer repositioning based on closed-loop feedback during use. The orientation may also be adjusted by the user based on her anatomy by using feedback from reflected ultrasound energy displayed in a user interface to assist in adjustment (e.g., blinking lights of different colors similar to a tuning instrument). The surface-to-surface interface between the transducer face and the coupling pad to maintain good acoustic coupling between surfaces can be achieved by adhesives, spring-loaded features, mechanical snap fits, and/or elastic materials (e.g., silicone or elastic band) that wrap around the back of the transducer. Ultrasound gel may also be applied to the interface between the transducer face and the coupling pad to enhance acoustic coupling.

In some embodiments, the device has features that provide feedback to the user regarding the quality and sufficiency of the contact between the transducer face and the coupling pad, and/or contact between the coupling pad the subject's tissue, for reasons, e.g., of the subject's safety, device integrity and efficacy of treatment. These feedback mechanisms can include simple feature locks that provide "snap" sounds to inform the user that the part is seated, impedance or other sensors between the transducer assembly and the coupling pad that provide direct feedback to the user, and/or alarms on the ultrasound generator that are based on sensor feedback. Such feedback can notify the user of inadequate and/or unsafe coupling between the transducer and the coupling structure, or inadequate and/or unsafe coupling between the coupling pad and the subject's tissue. Feedback may also be used to prevent the device from applying energy to the subject unless the device is assembled and applied in a manner providing sufficient acoustic coupling and to cease applying energy if the acoustic coupling ceases to be sufficient at some point during the therapy.

Embodiments of the device discussed above employ a coupling pad that does not penetrate the vagina. Ultrasound energy is applied to the subject's external anatomy near the vulva and the introitus through the coupling pad; the malleability of the coupling pad allows it to fill spaces between the transducer(s) and the tissue to provide adequate acoustic coupling so that ultrasound energy is effectively transmitted to the tissue. In other embodiments, the coupling member and even the ultrasound transducer may be inserted into the vagina.

The devices described with respect to FIGS. 1-3 may be used in a variety of ways to improve vaginal health. The device may be used on an as-needed basis prior to sexual relations to induce lubrication. The device may be used for between 30 seconds and 6 hours to induce enough lubrication for sexual intercourse. The device may also be used weekly, multiple times a week, daily or multiple times a day as a treatment or a preventative measure to improve overall vaginal health and rejuvenate the tissue (i.e., improving mucosal vascularity, restoring tissue elasticity, increasing constitutive lubrication, etc.). The device may also be used for shorter periods or longer periods of time. An automatic duty cycle or treatment algorithm may be employed to control overall energy delivery to the tissue and ensure safety while providing optimal therapy for desired outcomes. Alternatively, the device may be customized by the user to modify therapy as needed.

In some embodiments, the ultrasound therapy device described above may be used to treat vaginal atrophy and other conditions by generating and applying ultrasound to tissue around the subject's vagina at one or more frequencies between 0.5 MHz and 4 MHz, at intensities between 0.25 W/cm$^2$ and 5 W/cm$^2$, continuously or at a duty cycle in the range of 20%-80%. Variations may include the use of other ultrasound waveform parameters.

The device may have sensors embedded within the coupling pad for measurement of various physiologic parameters. These parameters may include mucosal/dermal blood flow (measure, e.g., with Doppler ultrasound, Doppler laser imaging, temperature or plethysmography); vaginal lubrication (e.g., using humidity sensors, absorbent materials or other methods for detecting lubrication and/or secretion); and other appropriate parameters. The sensors embedded with the device may allow for closed-loop feedback control of the therapy application.

For example, vulvar tissue temperature may be measured by a sensor in the coupling pad. If the temperature rises to a level that could potentially cause damage to the subject, the feedback loop would automatically adjust energy delivery parameters or even stop energy delivery. As another example, the device could increase energy delivery if the temperature of the subject's skin is not high enough. In yet another example, the device could measure physiologic outcome parameters (e.g., vaginal blood flow and/or lubrication) and automatically increase or decrease therapy delivery to achieve the desired outcome (e.g., vaginal blood flow and/or lubrication).

The device may be controlled, e.g., via buttons, dials, and/or a touchscreen interface on the generator or controller unit. A remote control may also be used to communicate control commands to a tabletop generator. The device may also integrate the generator, energy delivery unit and control interface. A mobile application may be used to control the device and/or obtain data regarding the device and its use.

A user interface providing data regarding the device and its use may be used for biofeedback based on measured physiologic parameters. The biofeedback may be structured in the form of a game whereby the subject elicits and augments physiologic responses to the energy applied by the device to the vulvovaginal tissues with additional biofeedback responses and/or nervous control.

Other control interfaces may allow more direct control of transducer function. Such a user interface via mobile platform technology can also be used with a wireless coupling pad to allow the user to control the device discreetly over the course of routine (and potentially continuous) use without having to directly handle the coupling pad or the generator.

The device may be portable, such as by being wearable. The device may contain a rechargeable energy source, such as batteries and/or a capacitor, that allows the user to use the device without being connected to line current. The ultrasound generator could be rechargeable and roughly the size of a smart phone or insulin pump to facilitate portability.

The device may be used at home, and the patient may be able to apply the therapy herself. The device may be designed in such a way to be conducive to one-hand self-application, or it may be entirely hands-free, while still maintaining proper tissue contact, orientation and treatment efficacy. Alternatively, the device and therapy may be applied by a partner.

Figure 4:
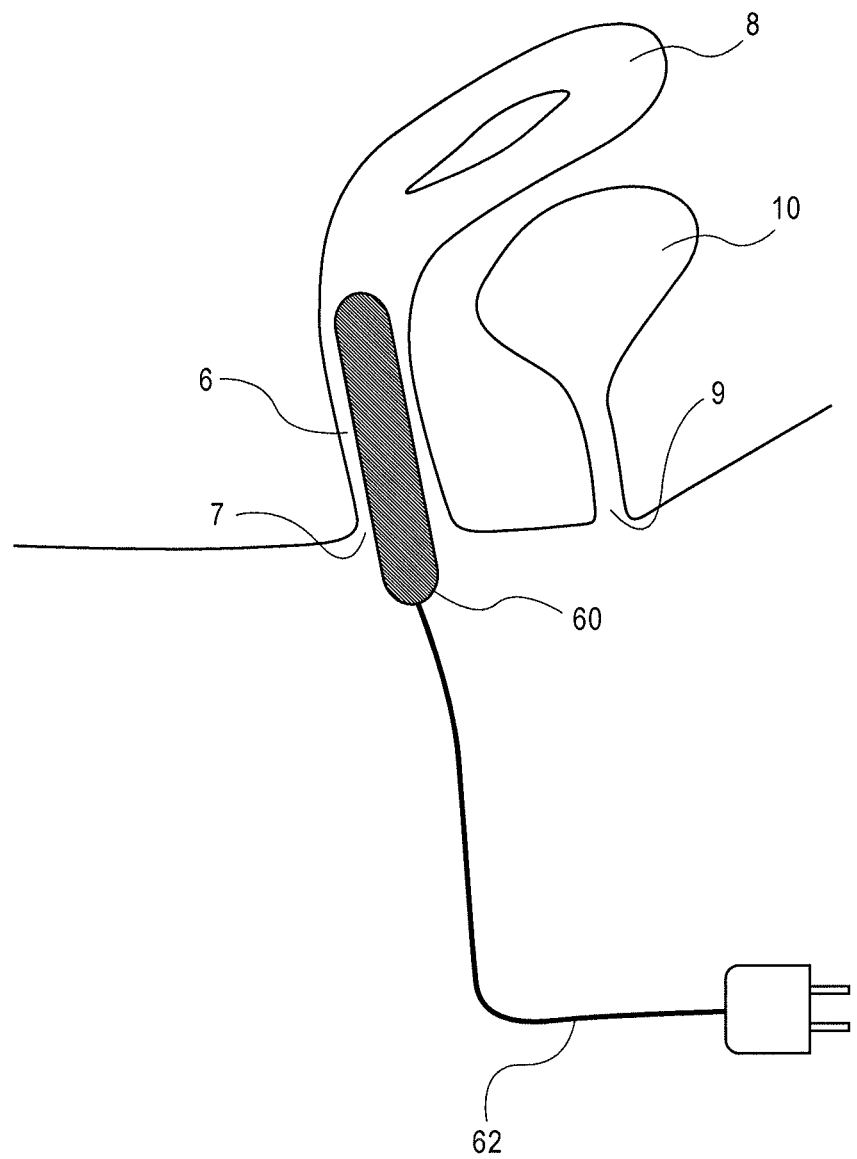
FIG. 4 is a partial cross-section view of yet another embodiment of a device according to the invention in position in a subject.

FIG. 4 shows an embodiment of the invention in which some of all of the device 60 is inserted into the vagina 6. As with the embodiments described above, energy may be applied acutely or on a continuous basis. The device may be controlled by an external device, powered by an external device or contain all power and control elements within the inserted element 60. In the embodiment shown in FIG. 4, the insertable energy delivery element 60 connects with an external energy source (not shown) via wire(s) 62.

Figure 5A:
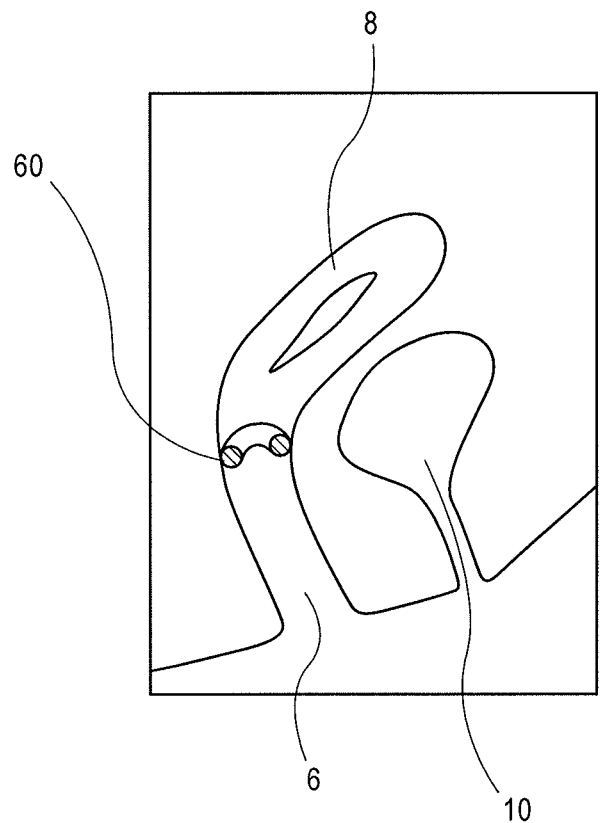
FIG. 5A is cross-sectional view of still another embodiment of a device according to the invention in position in a subject.
Figure 5B:
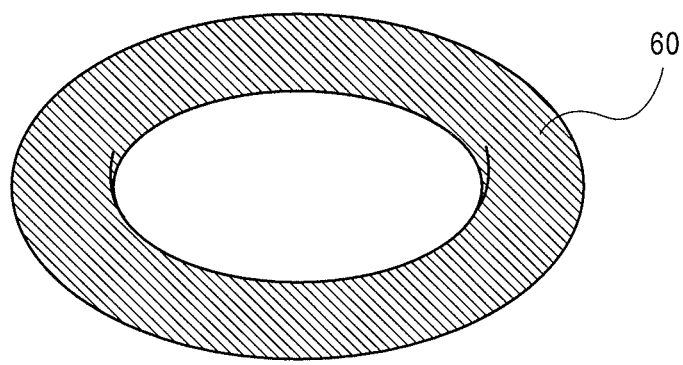
FIG. 5B is a perspective view of the device of FIG. 5A.

Insertable devices may be elongated, as shown in FIG. 4, ring-like, as shown in FIGS. 5A and 5B, or have other shapes, such as cylindrical, spherical, T-shaped, custom shaped to match the subject's vaginal cavity, etc. The insertable portion of the device may be inflatable, flexible and/or compressible for ease of insertion and for ensuring sufficient contact with the vaginal wall (made, e.g., of a biocompatible polymer like silicone or polyurethane), and it may attach to the vaginal wall (via, e.g., a mild, non-painful suction force). The device may be reusable or disposable. The energy applied by energy delivery element 60 may be some form of electric resistance heating, chemical heating, radiofrequency energy, ultrasound energy, vacuum/suction mechanical energy, photonic energy, electromagnetic radiation or other methods of transferring heat to tissue. For example, for ultrasound-based devices, the ultrasound may be delivered at one or more frequencies between 0.5 MHz and 4 MHz, at intensities between 0.25 $W/cm^2$ and 5 $W/cm^2$, continuously or at a duty cycle in the range of 20%-80%. A device that uses laser energy may utilize a pulsed laser or a continuous laser.

Figure 6:
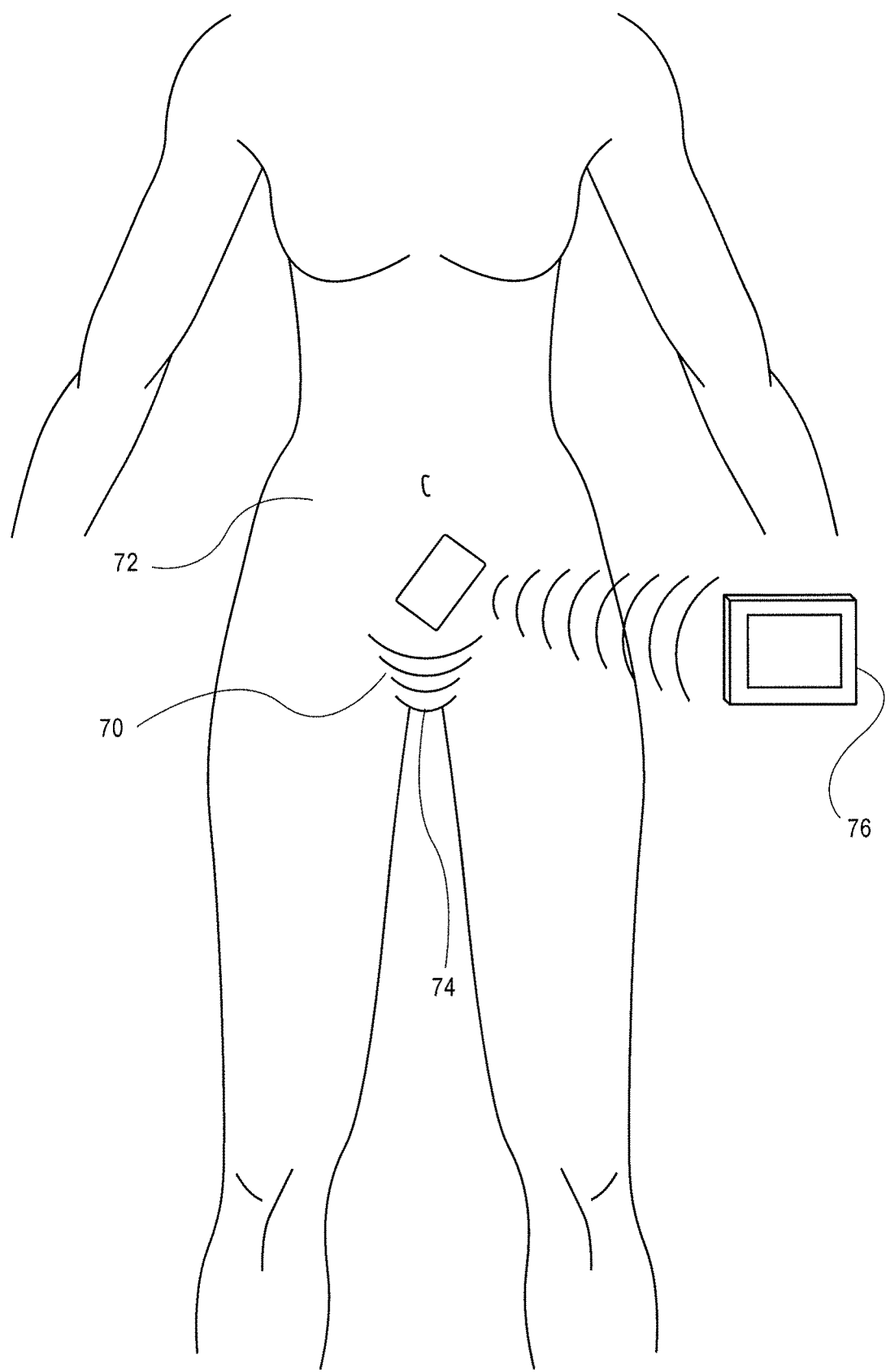
FIG. 6 is a perspective view of another embodiment of a device according to the invention in position on a subject.

FIG. 6 shows yet another embodiment of the invention in which an energy delivery element 70 (e.g., an ultrasound transducer and coupling medium) is in the form of a patch attached to the subject's abdomen or pelvis area 72. The energy delivery element is controlled by an external controller 76 to provide energy (such as ultrasound energy) to the subject's vagina and/or surround tissue 74. In embodiments employing ultrasound, the ultrasound waves may be focused or unfocused. The patch device may be reusable or disposable.

EXAMPLES

Example 1

Figure 7:
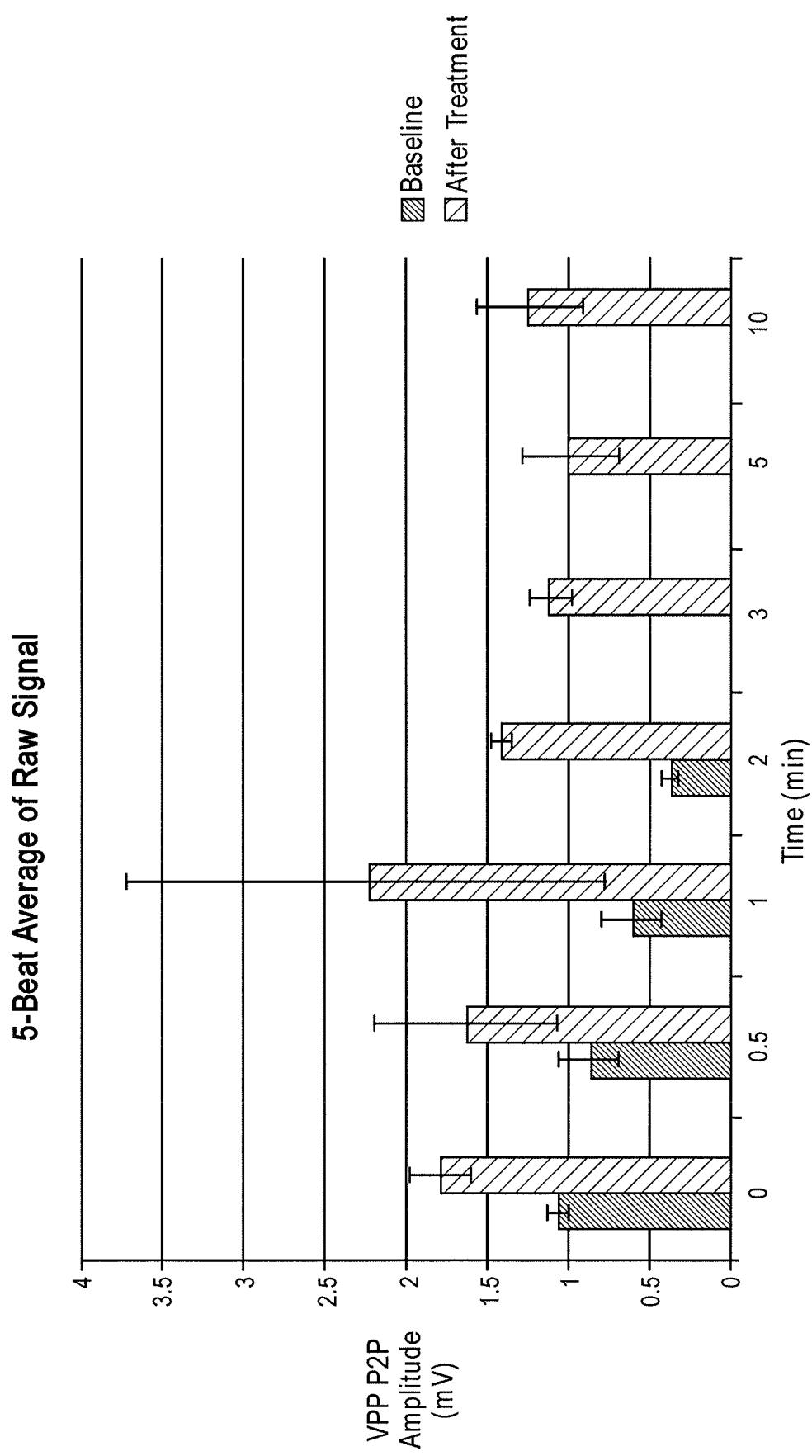
FIGS. 7, 8, 9 and 10 present data from use of the invention to treat subjects.
Figure 8:
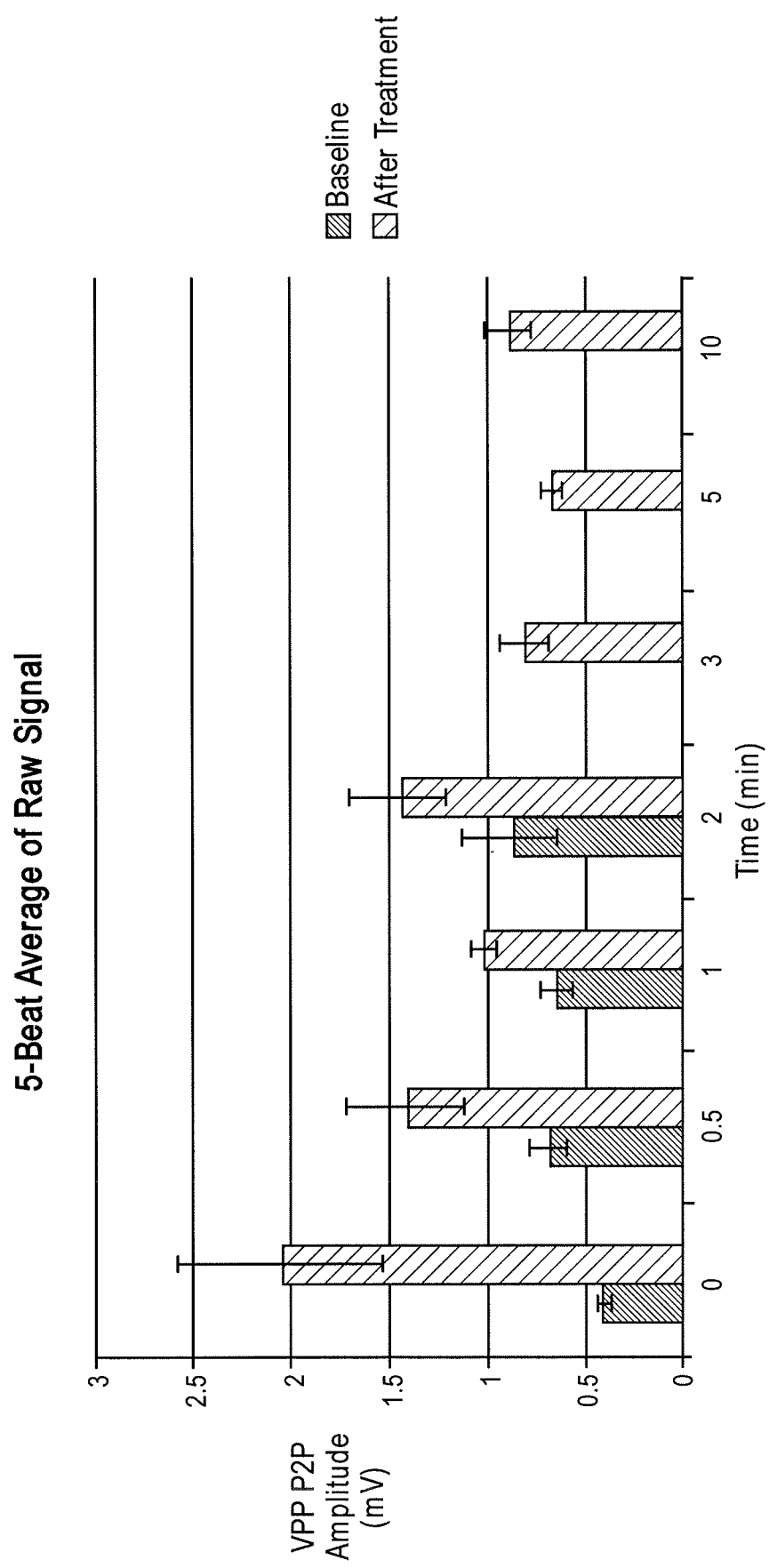

In a controlled study, the legs of two female subjects were placed in stirrups, and a baseline measurement of the blood pulse amplitude of the subjects' internal vaginal wall was measured with a vaginal plethysmography probe for two minutes. The beat average of the raw signals from the probes for the two subjects are plotted on FIGS. 7 and 8 as the first bar at each of times 0, 0.5 min, 1 minute and 2 minutes. A speculum exam was then performed on the subjects, and the plethysmography probe was once again used to measure the blood pulse amplitude in the subjects' vaginal tissue for two minutes (not shown in FIGS. 7 and 8). Thereafter, a condom filled with warm water and coated on both sides with a sonolucent gel was placed on each subject's vaginal area to cover her vulva and introitus, and an ultrasound transducer was placed against the condom. Ultrasound energy was introduced via the ultrasound transducer at 1 MHz, 1.5 $W/cm^2$ intensity, 50% duty cycle for 8 minutes. After the 8 minute treatment, the ultrasound transducer and condom were removed, and plethysmography measurements were obtained with the vaginal plethysmography probe at 0, 0.5 minutes, 1 minute, 2 minutes, 3 minutes, 5 minutes and 10 minutes after energy application ceased. The beat average of the raw signal from the probe for the two subjects are plotted on FIGS. 7 and 8 as the second bar at each of times 0, 0.5 min, 1 minute and 2 minutes and as the only bar at times thereafter. The increase in vaginal tissue blood pulse amplitude after treatment, and the persistence of this increase, shows the efficacy of the therapy in increasing blood flow to vaginal tissue.

Example 2

Figure 9:
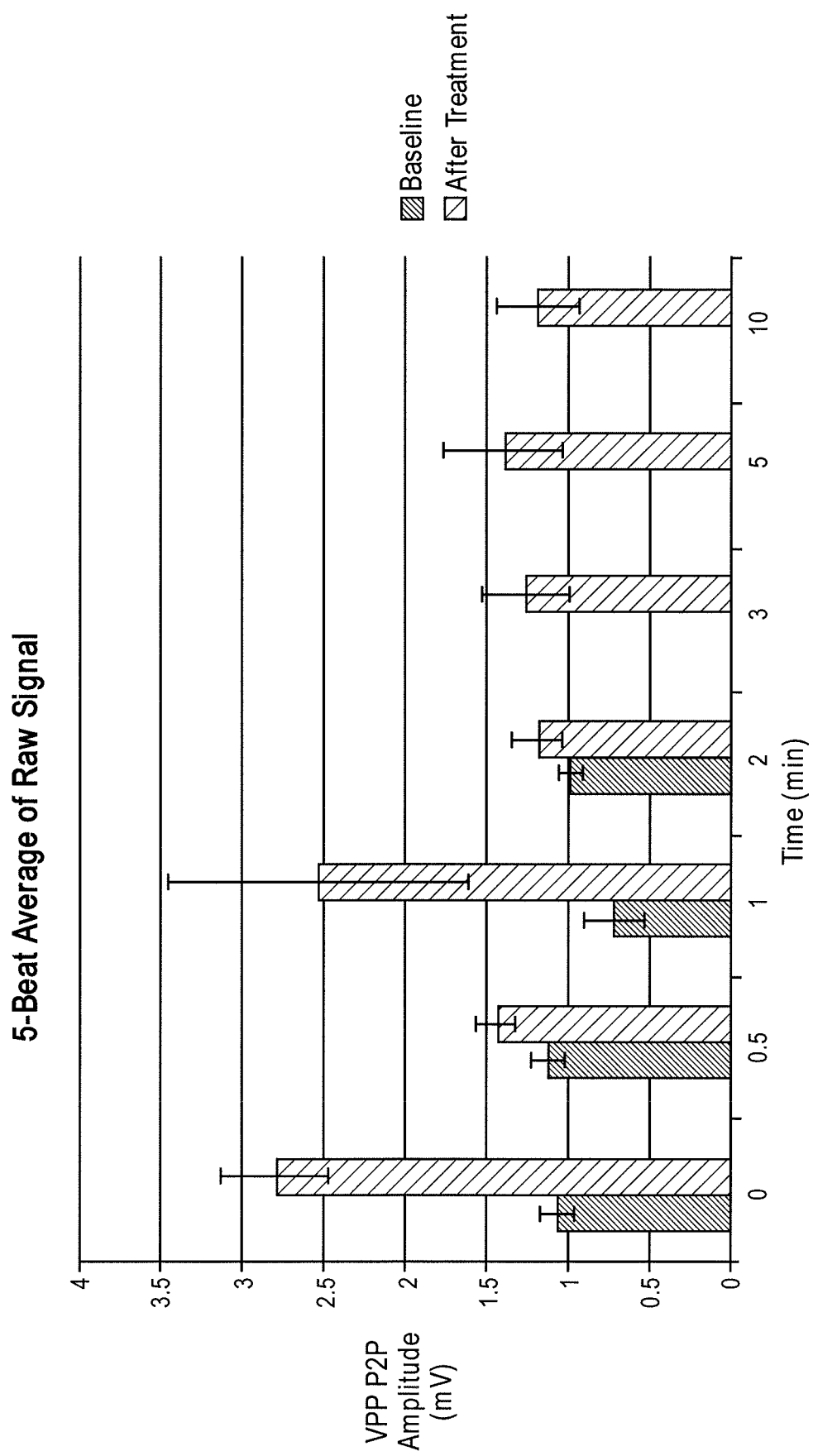

As in Example 1, the legs of a female subject were placed in stirrups, and a baseline measurement of the blood pulse amplitude of the subject's internal vaginal wall was measured with a vaginal plethysmography probe for two minutes. The beat average of the raw signal from the probe is plotted on FIG. 9 as the first bar at each of times 0, 0.5 min, 1 minute and 2 minutes. A speculum exam was then performed on the subject, and the plethysmography probe was once again used to measure the blood pulse amplitude in the subject's vaginal tissue for two minutes (not shown in FIG. 9). Thereafter, a condom filled with warm water and coated on both sides with a sonolucent gel was placed on the subject's vaginal area to cover her vulva and introitus, and an ultrasound transducer was placed against the condom.

Ultrasound energy was introduced via the ultrasound transducer at 1 MHz, 1.5 W/cm² intensity, 50% duty cycle for 8 minutes. After the 8 minute treatment, the ultrasound transducer and condom were removed, and plethysmography measurements were obtained with the vaginal plethysmography probe at 0, 0.5 minutes, 1 minute, 2 minutes, 3 minutes, 5 minutes and 10 minutes after energy application ceased (not shown in FIG. 9). The water-filled balloon was then re-applied to the subject's vaginal area to cover her vulva and introitus, and the ultrasound transducer was once again placed against the condom. Ultrasound energy was introduced via the ultrasound transducer at 1 MHz, 1.5 W/cm² intensity, 50% duty cycle for a second 8 minute treatment. After this second treatment, the ultrasound transducer and condom were removed, and plethysmography measurements were once again obtained with the vaginal plethysmography probe at 0, 0.5 minutes, 1 minute, 2 minutes, 3 minutes, 5 minutes and 10 minutes after the second energy application ceased. The beat average of the raw signal from the probe after the second ultrasound application is plotted on FIG. 9 as the second bar at each of times 0, 0.5 min, 1 minute and 2 minutes and as the only bar at times thereafter. The increase in vaginal tissue blood pulse amplitude after treatment, and the persistence of this increase, shows the efficacy of the therapy in increasing blood flow to vaginal tissue.

Example 3

Figure 10:
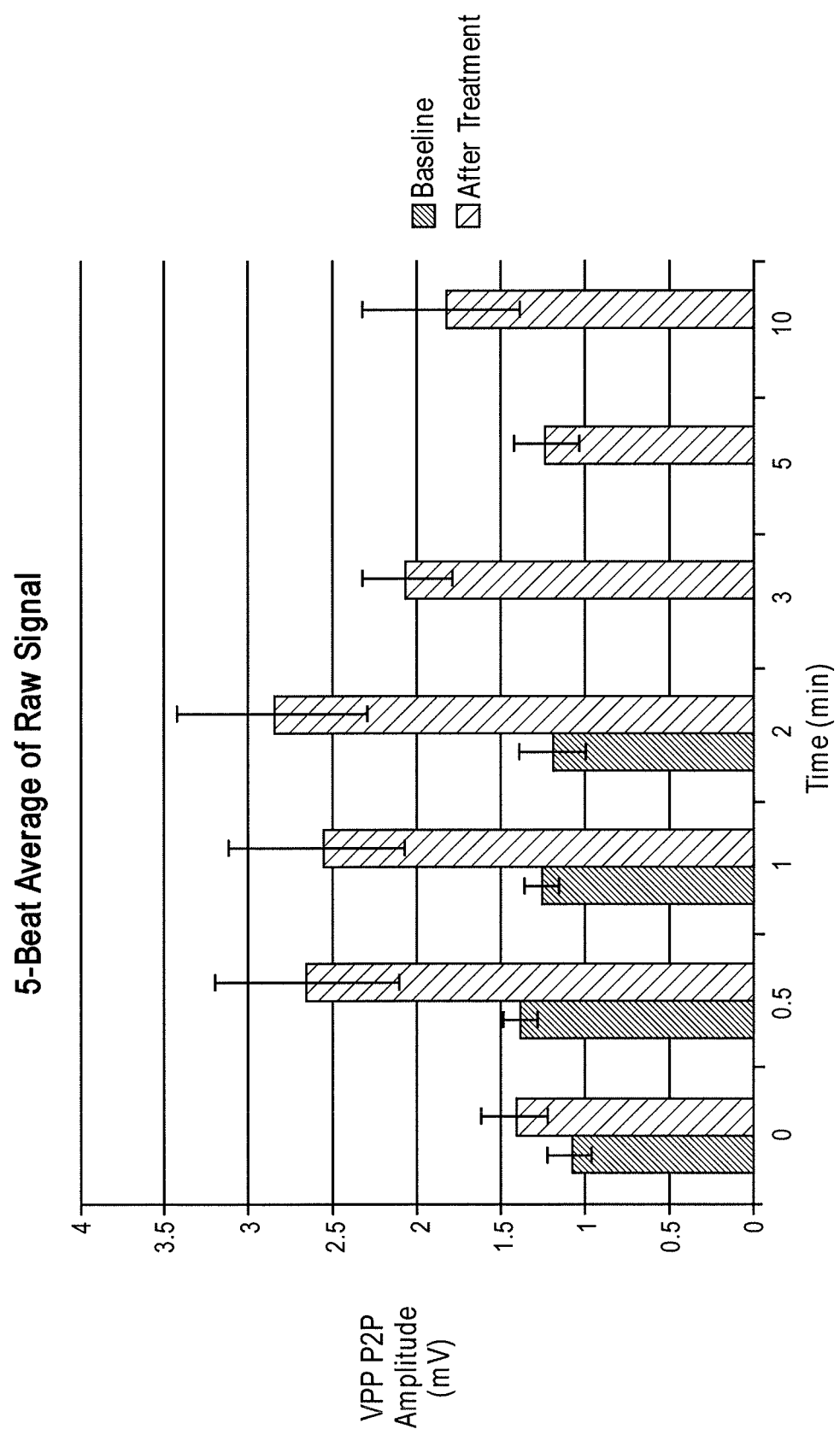

As in Examples 1 and 2, the legs of a female subject were placed in stirrups, and a baseline measurement of the blood pulse amplitude of the subject's internal vaginal wall was measured with a vaginal plethysmography probe for two minutes. A speculum exam was then performed on the subject, and the plethysmography probe was once again used to measure the blood pulse amplitude in the subject's vaginal tissue for two minutes (not shown in FIG. 10). The beat average of the raw signal from the probe after the speculum exam is plotted on FIG. 10 as the first bar at each of times 0, 0.5 min, 1 minute and 2 minutes. Thereafter, a condom filled with warm water and coated on both sides with a sonolucent gel was placed on each subject's vaginal area to cover her vulva and introitus, and an ultrasound transducer was placed against the condom. Ultrasound energy was introduced via the ultrasound transducer at 1 MHz, 1.5 W/cm² intensity, 50% duty cycle for 8 minutes. After the 8 minute treatment, the ultrasound transducer and condom were removed, and plethysmography measurements were obtained with the vaginal plethysmography probe at 0, 0.5 minutes, 1 minute, 2 minutes, 3 minutes, 5 minutes and 10 minutes after energy application ceased. The beat average of the raw signal from the probe is plotted on FIG. 10 as the second bar at each of times 0, 0.5 min, 1 minute and 2 minutes and as the only bar at times thereafter. The increase in vaginal tissue blood pulse amplitude after treatment, and the persistence of this increase, shows the efficacy of the therapy in increasing blood flow to vaginal tissue.

What is claimed is:

1. A method of treating vaginal tissue atrophy in a female subject, the method comprising:
    engaging an energy delivery element with tissue in or around the subject's vagina, the energy delivery element comprising an ultrasound transducer in contact with an ultrasound coupling medium, the engaging comprising conforming the energy delivery element to tissue in or around the subject's vagina;
    applying ultrasound energy at a frequency between 0.5 MHz and 4 MHz to the tissue from the energy delivery element, wherein the engaging the energy delivery element and the applying ultrasound energy are self administered by the subject; and
    increasing vaginal lubrication and blood flow to internal vaginal tissue to an increased level above a baseline level of blood flow to the internal vaginal tissue, the increased level of blood flow to the internal vaginal tissue persisting after the applying step ceases.

2. The method of claim 1 wherein the energy delivery element comprises an ultrasound probe.

3. The method of claim 1 wherein the applying step comprises applying ultrasound energy at an intensity between 0.25 W/cm² and 5 W/cm².

4. The method of claim 1 wherein the applying step comprises applying ultrasound energy at a duty cycle in a range of 20%-80%.

5. The method of claim 1 wherein the applying step comprises applying ultrasound energy for a period between 30 seconds and 6 hours.

6. The method of claim 1 wherein the engaging step comprises conforming the energy delivery element to the subject's vulva and introitus.

7. The method of claim 6 wherein the engaging step comprising engaging the ultrasound coupling medium to the subject's tissue.

8. The method of claim 1 wherein the engaging step comprises engaging the energy delivery element with tissue inside the subject's vagina.

9. The method of claim 1 wherein the engaging step comprises engaging the energy delivery element with tissue of the subject's abdomen or pelvis.

10. The method of claim 1 further comprising measuring a physiologic parameter of the subject's tissue in or around the subject's vagina and controlling energy delivery from the energy delivery element based on the measured parameter.

11. The method of claim 10 wherein the parameter is temperature, blood flow or vaginal lubrication.

12. A device for treating vaginal tissue atrophy in a female subject, comprising:
    an energy delivery element comprising an ultrasound coupling medium and adapted to conform to tissue in or around the subject's vagina; and
    an ultrasound transducer adapted to deliver energy to the energy delivery element to increase vaginal lubrication and blood flow to internal vaginal tissue to an increased level above a baseline level of blood flow to the internal vaginal tissue such that the increased level of blood flow to the internal vaginal tissue persists after energy application ceases, the ultrasound transducer comprising an ultrasound generator adapted to provide ultrasound energy at a frequency between 0.5 MHz and 4 MHz, the ultrasound transducer in contact with the ultrasound coupling medium, wherein the device is configured for self application.

13. The device of claim 12 wherein the ultrasound generator is adapted to provide ultrasound energy at an intensity between 0.25 W/cm² and 5 W/cm².

14. The device of claim 12 wherein the ultrasound generator is adapted to provide ultrasound energy at a duty cycle in a range of 20%-80%.

15. The device of claim 12 wherein the ultrasound coupling medium is disposed within a container adapted to cover a vaginal opening and tissue around the vaginal opening.

16. The device of claim 15 wherein the container is adapted to conform to the subject's tissue.

17. The device of claim 12 wherein the ultrasound coupling medium comprises gel on a surface of the energy delivery element.

18. The device of claim 12 wherein the energy delivery element is adapted to engage tissue exterior to the subject's vagina.

19. The device of claim 12 wherein the energy delivery element is adapted to engage tissue inside the subject's vagina.

20. The device of claim 12 wherein the energy delivery element is adapted to engage tissue of the subject's abdomen or pelvis.

21. The device of claim 12 further comprising a sensor adapted and configured to measure a physiologic parameter of tissue in or around the subject's vagina when the energy delivery element is engaged with tissue in or around the subject's vagina, the device being further configured to use information from the sensor to control energy delivery from the energy delivery element.

22. The device of claim 21 wherein the physiologic parameter is temperature, blood flow or vaginal lubrication.

23. The method of claim 1, wherein engaging an energy delivery element with tissue in or around the subject's vagina comprises engaging the ultrasound coupling medium with tissue in or around the subject's vagina.

\* \* \* \* \*